US009235681B2

(12) United States Patent
Smith (10) Patent No.: US 9,235,681 B2
(45) Date of Patent: Jan. 12, 2016

(54) SYSTEM AND METHOD FOR INTERSYSTEM DEVICE EXCHANGE

(75) Inventor: Todd Edward Smith, Hopedale, MA (US)

(73) Assignee: Smith & Nephew, Inc., Memphis, TN (US)

( * ) Notice: Subject to any disclaimer, the term of this patent is extended or adjusted under 35 U.S.C. 154(b) by 350 days.

(21) Appl. No.: 13/252,392

(22) Filed: Oct. 4, 2011

(65) Prior Publication Data

US 2013/0086162 A1 Apr. 4, 2013

(51) Int. Cl.
*G06F 15/16* (2006.01)
*G06F 19/00* (2011.01)
*H04L 12/64* (2006.01)

(52) U.S. Cl.
CPC ........ *G06F 19/3406* (2013.01); *G06F 19/3418* (2013.01); *H04L 12/6418* (2013.01)

(58) Field of Classification Search
CPC ............ H04L 12/6418; G06F 19/3406; G06F 19/3418; H04W 12/00
USPC ................. 709/224, 201, 229, 227, 238, 245; 707/100; 370/401, 260
See application file for complete search history.

(56) References Cited

U.S. PATENT DOCUMENTS

| 678,573 | A |   | 7/1901  | King            |         |
|---------|---|---|---------|-----------------|---------|
| 4,777,595 | A | * | 10/1988 | Strecker et al. | 709/236 |
| 5,410,471 | A | * | 4/1995  | Alyfuku et al.  | 600/300 |
| 6,549,951 | B1 | * | 4/2003 | Hui et al.      | 709/250 |
| 6,859,831 | B1 | * | 2/2005 | Gelvin et al.   | 709/224 |
| 6,938,089 | B1 | * | 8/2005 | Slaby et al.    | 709/229 |
| 6,965,614 | B1 | * | 11/2005 | Osterhout et al.| 370/466 |
| 7,002,964 | B1 | * | 2/2006 | Ohnishi et al.  | 370/395.2 |
| 7,191,238 | B2 | * | 3/2007 | Uchida          | 709/229 |
| 7,526,789 | B2 | * | 4/2009 | Bizet           | 725/119 |
| 7,630,371 | B2 | * | 12/2009 | Hernandez et al.| 370/392 |

(Continued)

FOREIGN PATENT DOCUMENTS

JP 2001236421 8/2001
WO WO2010035165 4/2010

OTHER PUBLICATIONS

International Search Report from corresponding International Application No. PCT/US2012/058509 mailed Jul. 26, 2013.

*Primary Examiner* — Viet Vu
*Assistant Examiner* — Michael A Chambers
(74) *Attorney, Agent, or Firm* — Chapin IP Law, LLC (57) ABSTRACT

A device exchange transports messages between autonomous devices in a medical environment. The autonomous devices perform various tasks in the medical environment, such as surgical device control, drug infusion, video recordation, and user interfaces, for example. Each autonomous device has a device specification, published and stored by the device exchange and available to other autonomous devices. The device specification indicates, for each autonomous device, an identifier, a set of outputs and a set of inputs, or commands. Devices interoperate by messages including the device identifier and an output or command without translation or transformation mechanisms such as scripts, protocol translations, drivers or interface modules because each message is based on the published device specification available to all the devices connected to the exchange. Interconnected medical devices therefore interoperate without the need for reconfiguration because each device has internal logic for understanding the messages it sends and receives via the exchange.

18 Claims, 6 Drawing Sheets

(56) References Cited

U.S. PATENT DOCUMENTS

| | | | |
|---|---|---|---|
| 7,676,613 B2* | 3/2010 | Bashford et al. | 710/74 |
| 7,894,383 B2* | 2/2011 | Ikeda et al. | 370/328 |
| 7,937,163 B2* | 5/2011 | Sekiguchi | 700/17 |
| 8,126,728 B2* | 2/2012 | Dicks et al. | 705/2 |
| 8,200,818 B2* | 6/2012 | Freund et al. | 709/225 |
| 8,265,089 B2* | 9/2012 | McCoy et al. | 370/401 |
| 8,509,260 B2* | 8/2013 | Koenck et al. | 370/466 |
| 8,555,273 B1* | 10/2013 | Chia et al. | 717/173 |
| 8,736,661 B2* | 5/2014 | Koh et al. | 348/14.08 |
| 2001/0031913 A1* | 10/2001 | Ito et al. | 600/300 |
| 2002/0133595 A1* | 9/2002 | Kimura et al. | 709/227 |
| 2003/0055962 A1* | 3/2003 | Freund et al. | 709/225 |
| 2003/0188028 A1* | 10/2003 | Kawamura | 709/249 |
| 2004/0030582 A1* | 2/2004 | Kerr, II | 705/2 |
| 2004/0132437 A1* | 7/2004 | Ohmori et al. | 455/414.1 |
| 2004/0167804 A1* | 8/2004 | Simpson et al. | 705/3 |
| 2005/0066002 A1* | 3/2005 | Teres et al. | 709/204 |
| 2005/0066039 A1* | 3/2005 | Ayatsuka et al. | 709/228 |
| 2005/0113648 A1 | 5/2005 | Yang et al. | |
| 2005/0216483 A1* | 9/2005 | Armstrong et al. | 707/100 |
| 2005/0222691 A1* | 10/2005 | Glas et al. | 700/19 |
| 2006/0080380 A1* | 4/2006 | Aizu et al. | 709/203 |
| 2006/0111936 A1* | 5/2006 | Mahesh et al. | 705/2 |
| 2006/0209884 A1* | 9/2006 | MacMullan et al. | 370/465 |
| 2006/0209892 A1* | 9/2006 | MacMullan et al. | 370/468 |
| 2006/0267857 A1* | 11/2006 | Zhang et al. | 345/1.1 |
| 2007/0276956 A1* | 11/2007 | Dorai et al. | 709/238 |
| 2008/0044018 A1* | 2/2008 | Scrimsher et al. | 380/210 |
| 2008/0235399 A1* | 9/2008 | Maekawa et al. | 709/245 |
| 2008/0261509 A1* | 10/2008 | Sen | 455/1 |
| 2009/0276515 A1* | 11/2009 | Thomas et al. | 709/223 |
| 2009/0287857 A1* | 11/2009 | Vu | 710/22 |
| 2009/0292340 A1 | 11/2009 | Mass et al. | |
| 2010/0197265 A1* | 8/2010 | Dorenbosch et al. | 455/404.1 |
| 2010/0208647 A1* | 8/2010 | Nagao et al. | 370/315 |
| 2011/0058562 A1* | 3/2011 | McCoy et al. | 370/401 |
| 2012/0023239 A1* | 1/2012 | Fan et al. | 709/227 |
| 2012/0303586 A1* | 11/2012 | Drath et al. | 707/649 |

* cited by examiner

SYSTEM AND METHOD FOR INTERSYSTEM DEVICE EXCHANGE

BACKGROUND

Modern medical technology is continually introducing new and more sophisticated medical devices for surgical, diagnostic, patient monitoring and medicine dispensation, to name several. There may be several devices employed simultaneously for a particular patient or procedure. Often, devices are interconnected for providing complementary control, feedback and/or diagnostic information to other devices or to medical personnel. As technology and health care costs continue to evolve, the demand for greater performance and lower cost encourages market entry by additional medical device vendors. Medical personnel therefore confront a broad spectrum of device options for consideration in a particular patient or procedure context. Accordingly, the same patient or procedure may benefit from procedures employing devices of different vendors.

SUMMARY

A device exchange transports messages between autonomous devices in a medical environment. The autonomous devices perform various tasks in the medical environment, such as surgical device control, drug infusion and delivery, video recordation, and user interfaces, for example. Each autonomous device has a device specification, published and stored by the device exchange and available to other autonomous devices. The device specification indicates, for each autonomous device, an identifier, a set of outputs and a set of inputs, or commands. Devices interoperate by messages including the device identifier and an output or command without translation or transformation mechanisms such as scripts, protocol translations, drivers or interface modules because each message is based on the published device specification available to all the devices connected to the exchange. Interconnected medical devices therefore interoperate without the need for scripts, drivers, protocol translators or extensive configuration because each device has internal logic for understanding the messages it sends and receives via the common device exchange (exchange).

The disclosed approach provides not only access and interfaces between the local autonomous devices, but also provides a homogenous interface to other remote devices, monitor platforms, control platforms, and user interfaces. This provides a portal for such possibilities for remote diagnostics, remote updates, compliance tasks, e-commerce, server for shared application or services, and interface to electronic health record systems. The disclosed approach also embodies the concept of gateways or interfaces of legacy equipment to the exchange.

Configurations herein are based, in part, on the observation that conventional device interconnections typically employ a device specific link that incorporated a conversion or translation to adapt the inputs and outputs of each device. Scripts, protocol translators, drivers or the like need to be configured and invoked to enable interoperability. Often, a specific protocol is created to exchange very basic data or actions between two devices through a serial connection. Conventional integration and interoperability focus on the concept of unique device interfaces which are formally scripted in a limited point-to-point interface, typically for only rudimentary operations which are extensively scripted to meet specific devices, needs and actions. The interfaces are typically not asynchronous and are highly specific to the devices and controllers, and are such that modifications to one device interface require changes to the software of both devices. It would be beneficial to provide an interface structure which is common, and able to be populated by each device.

Unfortunately, therefore, conventional approaches to device interconnection suffer from the shortcoming that medical devices frequently conform to a proprietary control scheme known only to the particular vendor of the device, thus encouraging repeat purchases by streamlining interconnection to the vendor's devices and requiring reconfiguration for cross-vendor integration. The result is often that control and other data exchanges between conventional devices frequently use point-to-point or secondary controllers to drive basic information and actions. These actions are typically rudimentary and are highly scripted to meet specific devices, needs and actions. Such links are frequently serial and point to multipoint point or one-to-one. Devices frequently do not communicate via a common manner or interface and modifications to one device interface require changes to the software of both devices.

Accordingly, configurations herein substantially overcome the above described shortcomings by publishing a device specification to a device exchange visible to each of the connected autonomous devices. Each autonomous device retains logic for identifying the published device specification of other devices with which it may converse. Each autonomous device can identify and receive messages published on the exchange. A device identifier in the device specification ensures that messages transmitted on the device exchange are read by the intended recipient device. The device exchange therefore not only facilitates inter-device communication but serves as a portal to provide a robust exchange of information in the most generic fashion and also to provide a repository data of a transient, permanent or archival nature via a connected database. Each device connects to the exchange via generic protocol in which it reveals to the exchange the nature of its interface and data. The common device description exchange provides a generic and common structure so that the data can be shared at a common level by the interconnected autonomous devices. A "lightweight" version further streamlines the device specification and exchange to suit two or 3 highly coupled devices, and resident on one or more of the devices.

In a particular configuration, the exchange operates as a clearinghouse between connected devices such that devices register by sending their device specification, and the exchange transmits or forwards updates to the device specification upon receiving changes. Exchange logic indicates, based on the type of device, which devices are "interested in," or are intended to receive updates from. Connected devices transmit an updated device specification to the exchange upon a change in one or more parameters, and the exchange sends the updated device specification to interested devices. For example, in a pump and shaver system, the pump sends its device specification to the exchange upon startup. The shaver does the same. The exchange logic identifies the shaver as a device associated with the pump, and sends the pump updates to the device specification of the shaver so that the pump may adjust flow accordingly.

The exchange operates according to an underlying transport medium, which may include, for example, TCP/IP, UDP, Ethernet, or other transport medium, however the communication between the devices and the exchange is based on the device specification of each respective device.

In further detail, the method of control and data exchange between autonomous devices includes receiving, from each of a plurality of autonomous devices, a device specification, such that the device specification defines a device identifier, receivable commands and device outputs, and storing, for each device of the plurality of autonomous devices, the device specification in a repository connected to a device exchange interconnecting each of the autonomous devices. The exchange publishes each of the stored device specification for receipt by at least one other of the autonomous devices, such that each autonomous device may transmit, based on the published device specification, a message including a command or a device output from one of the autonomous devices to a destination device of the autonomous devices. The transmission is an unscripted exchange initiated by the transmitting autonomous device for receipt by the destination device based on the published device specification from the destination device.

Alternate configurations of the invention include a multi-programming or multiprocessing computerized device such as a workstation, handheld or laptop computer or dedicated computing device or the like configured with software and/or circuitry (e.g., a processor as summarized above) to process any or all of the method operations disclosed herein as embodiments of the invention. Still other embodiments of the invention include software programs such as a Java Virtual Machine and/or an operating system that can operate alone or in conjunction with each other with a multiprocessing computerized device to perform the method embodiment steps and operations summarized above and disclosed in detail below. One such embodiment comprises a computer program product that has a non-transitory computer-readable storage medium including computer program logic encoded as instructions thereon that, when performed in a multiprocessing computerized device having a coupling of a memory and a processor, programs the processor to perform the operations disclosed herein as embodiments of the invention to carry out data access requests. Such arrangements of the invention are typically provided as software, code and/or other data (e.g., data structures) arranged or encoded on a computer readable medium such as an optical medium (e.g., CD-ROM), floppy or hard disk or other medium such as firmware or microcode in one or more ROM, RAM or PROM chips, field programmable gate arrays (FPGAs) or as an Application Specific Integrated Circuit (ASIC). The software or firmware or other such configurations can be installed onto the computerized device (e.g., during operating system execution or during environment installation) to cause the computerized device to perform the techniques explained herein as embodiments of the invention.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Depicted below is an example configuration of a medical device environment employing autonomous devices connected to the device exchange (exchange) in conjunction with the approaches outlined herein. In a particular configuration, the exchange may take the form of an Ethernet bus connected to a server for monitoring and managing the exchange. Connected devices therefore employ Ethernet connections for sending and receiving messages. In contrast to conventional approaches, the Ethernet access is asynchronous, rather than packet switched, such that all devices may receive a message or publication simultaneously from any of the other devices. The common structure of the device specification provides autonomous or asynchronous? messages, such that connected devices transfer messages upon an event or change, rather than as a periodic (possibly redundant) polling or multicast transmission. Further, since each message defined by the device specification comprises a contiguous, single level (non-hierarchical) structure, extensive parsing and conditional interpretation of hierarchical nested fields is avoided as each message follows the corresponding device specification stored in the exchange, thus avoiding version or type mismatches common with protocol based exchanges. The disclosed approach thus avoids multiple levels of "layering" common to protocols, but rather employs the exchange for defining the field structure (i.e. length).

The device exchange therefore provides a communication link between multiple devices made by a plurality of collaborative OEMS (original equipment manufacturers). The device exchange may be implemented as a software service in a minimal deployment and/or a combination software and hardware appliance(s) in an enterprise environment. The disclosed device exchange provides the ability of a sharing of information, control and data across the exchange for all interconnected devices to access via the published device specification. The exchange is intended to provide not only access and interfaces between devices, but to provide a homogenous interface to other devices, monitor platforms, control platforms, and user interfaces. This approach provides a portal for configurations including remote diagnostics, remote updates, compliance tasks, e-commerce, a server for shared application or services, and interfaces to electronic health record systems. Alternate configurations embrace the concept of gateways or interfaces of legacy equipment to the exchange.

The resulting data exchange not only facilitates inter-device communication but serves as a portal to provide a robust exchange of information in the most generic fashion, and also to provide a repository for data of a transient, permanent or archival nature. Each device connects to the exchange via a generic format in which it reveals to the exchange the nature of its interface and data by the device specification. The format employed by the exchange provides a generic and common structure via the device specification so that the data can be shared at a common level. The published data and interface, once on the exchange, can be ported to multiple local interface devices and those across the web, for example.

In the proposed approach, the autonomous devices employ a common device specification instead of a script or protocol conversion for identifying and responding to communications from others of the autonomous devices. The common device specification has a readily identifiable format of an identifier, list of outputs and list of commands (inputs). The common device specification may differ from protocol or TLV (Type, Length, Value) based input because each field is specified by the device specification and may be read asynchronously from the common exchange by each device so connected. Each autonomous device identifies and interprets only messages intended for itself by matching the device identifier with messages published from the other autonomous devices.

Conventional serial or packet switched mediums define a payload and header, and may subdivide a message or payload according to a protocol specified structure for transmission as a payload in a sequence of packets. In contrast, the claimed commands and outputs define transmissions based on the device specification, rather than an external protocol specification. Since each message to or from a device is based on the published device specification, there need not be position specific identifiers for indexing fields within the message. The device specification does not require a driver or iterative conversion for identifying and interpreting messages from other devices. While protocols typically use layers of rule based fields superimposed on a string of bits, the disclosed approach is layerless in that the messages are defined based on a flat, single level device specification, in contrast to multiple embedded protocols that populate a single payload. Since the device specification (and not a protocol) specifies the structure, a recipient need only look to the device specification, and need not decode embedded fields in the message (some protocols embed entire messages in a payload of another packet for tunneling and similar operations). At a minimum, the device specification includes a device identifier, a device type, a heartbeat and an input/output definition indicative of other (possibly optional) fields in the device specification. While single packet messages are likely, the exchange does not preclude multiple packet messages. Periodic messages including the heartbeat may be sent, however the exchange is generally event based, meaning that messages identify when the device specification changes, or a response to such a change, and status quo is otherwise assumed.

Figure 1:
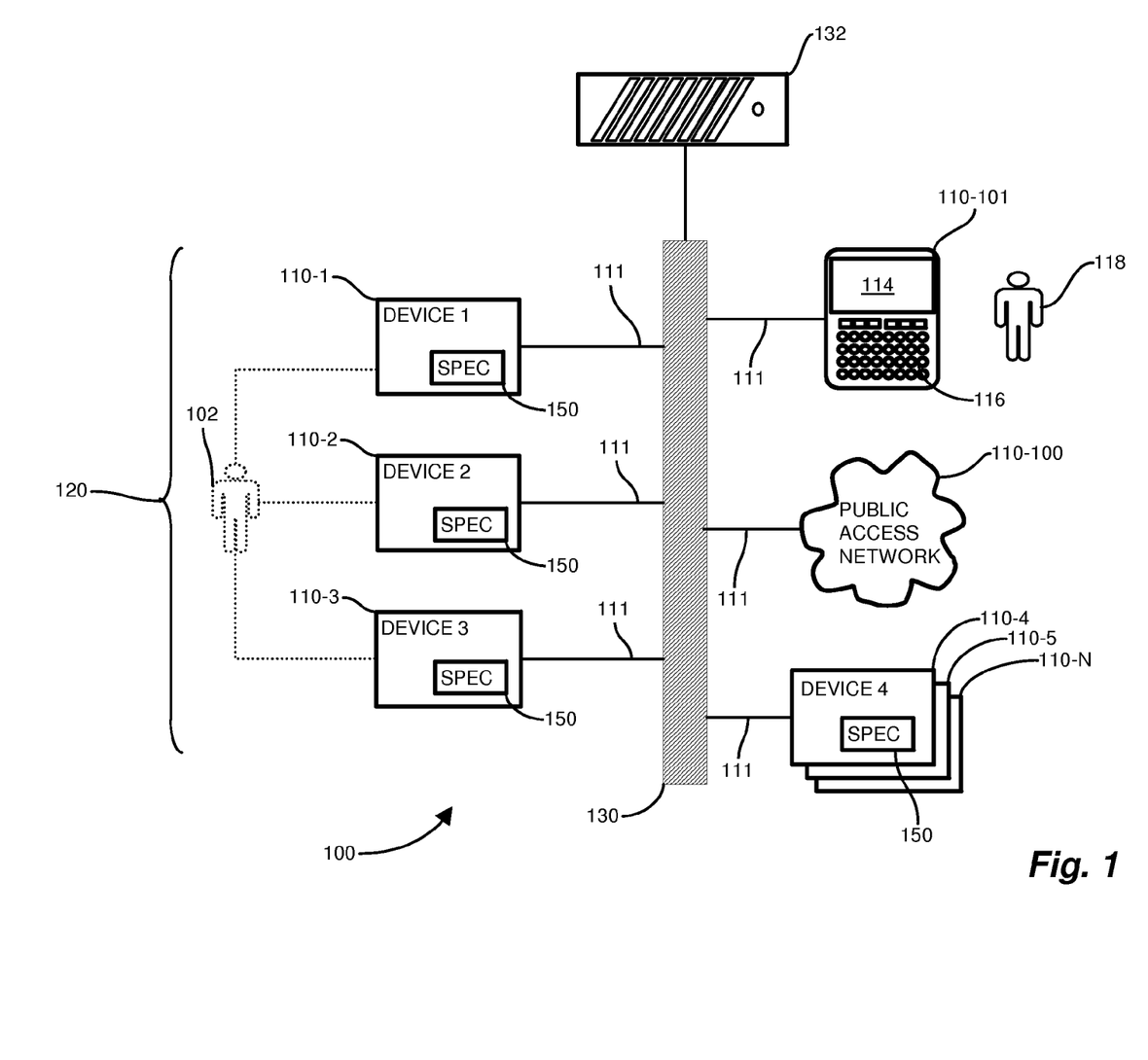
FIG. 1 is a context diagram of a medical device environment suitable for use with configurations disclosed herein.

FIG. 1 is a context diagram of a medical device environment 100 suitable for use with configurations disclosed herein. Referring to FIG. 1, in a medical device environment 100, such as a hospital or doctor's office, a medical staff employs a variety of autonomous devices 110-1 . . . 110-N (110 generally) during the care of a patient 102. The autonomous devices (devices) 110 include, for example, surgical tools, monitoring and diagnostic sensors, and audio/visual feedback equipment. Each of the devices 110 connects to the device exchange 130, which is responsive to a network appliance such as a server 132 for providing communications between the entities connected thereto. The network appliance 132 may be a software application and/or hardware based application for providing transport and storage services to the devices 110 connected to the device exchange (exchange), as discussed further below. Each device 110 includes an interface 111 to the exchange 130, which may be a coaxial cable connection, an RJ45 modular connector, an RS-232 (multi pin) connection, or other suitable connection. The devices 110 may also include a gateway 110-100 to a public access network such as the Internet, and an operator GUI (graphical user interface) 110-101 having a display 114 and keyed entry 116 responsive to medical personnel 118.

In an example arrangement as disclosed, the exchange 130 operates as an asynchronous bus which may be written to and read by each connected device 110. Each device 110 has a device specification 150 including a unique device identifier for designating the sender and recipient device. In a particular configuration, the exchange 130 operates as a carrier sense, multiple access collision detect (CSMACD) medium, meaning that each device 110 may attempt to transmit, every other device may "see" the transmission, and each device will respond to messages having a matching device identifier. If multiple devices attempt to transmit simultaneously, a collision detect feature identifies the collision and each device backs off for a differing interval to retry.

Alternate configurations may employ an alternate transport medium. The exchange 130 receives a corresponding device specification 150 from each device 110 and publishes it to every other device 110 such that only the device specification 150 of a destination device 110 is needed for communication, in lieu of interface modules, scripted exchanges and/or protocol translations. Messages between devices are effectively sent via the exchange 130, as the exchange receives a current device specification 150 from each autonomous device 110, stores it in the repository, and sends a message including the current device specification 150 when requested by an interested device 110. Thus, while each autonomous device 110 could receive a message including a device specification 150 from every other device 110, the rules and device control logic of each device identify which devices each is interested in. A pump is interested in a shaver, and thus receives messages to evaluate pump speed, while the pump would not need to receive messages from a medication infusion device, for example. Each device therefore "publishes" a device specification to the exchange for receipt by interested "subscribers" (devices having control logic based on the device specification 150), which the exchange sends upon each change to the device specification (based on events of the publishing device).

The exchange 130 includes a repository for performing data base functions by storing a current device specification for each device, and an interface module for defining logic, or rules, concerning interaction between the autonomous devices. The interface module of the exchange will not only establish and verify the rules, maintain the "heartbeat," but also manage the commands to the device and enforce rules. It will also serve to link devices logically, for example once a link has been requested and established between 2 or more devices the exchange will automatically push updates (data, connection status) to the linked devices, thereby eliminating polling for data and eliminating multiple connections to each device.

Figure 2:
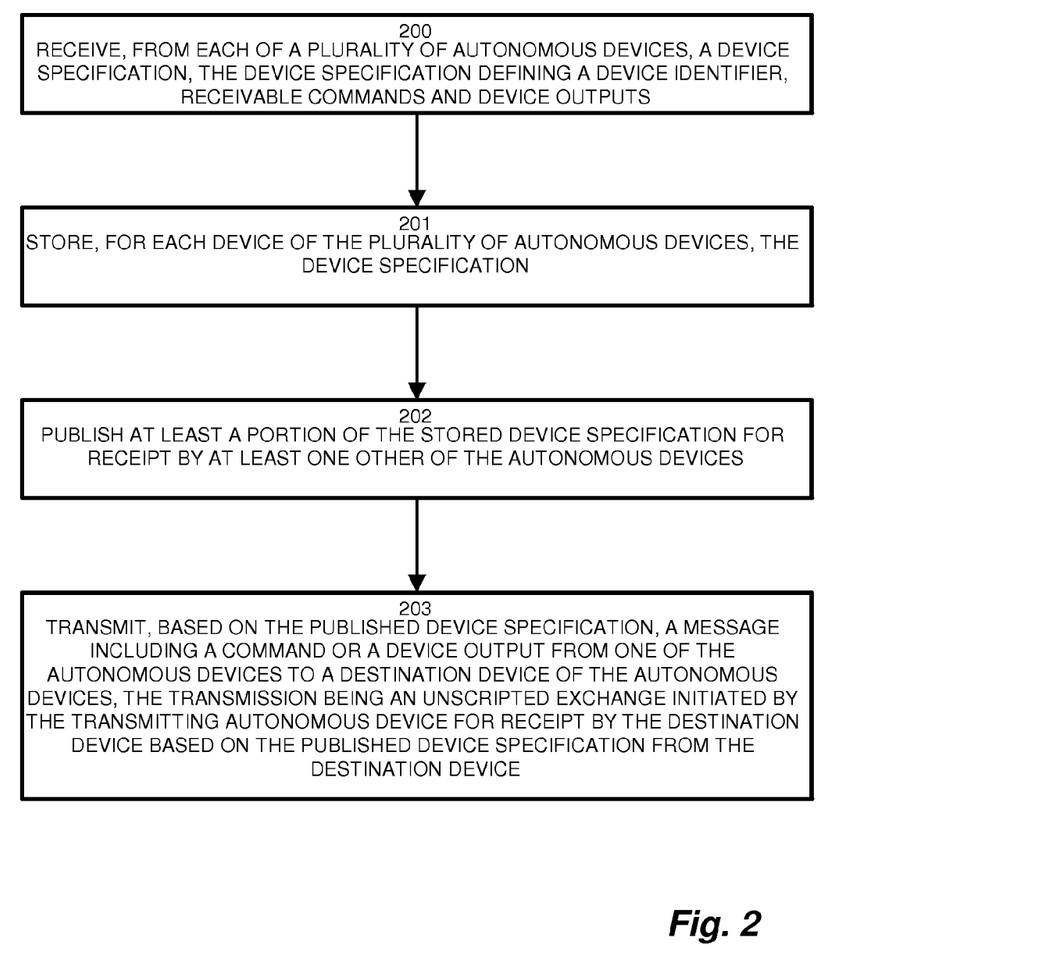
FIG. 2 is a flowchart of intersystem device exchange of control and data in the environment of FIG. 1.

FIG. 2 is a flowchart of intersystem device exchange of control and data in the environment of FIG. 1. Referring to FIGS. 1 and 2, the method of control and data exchange between autonomous devices 110 includes, at step 200, receiving, from each of a plurality of autonomous devices 110, a device specification 150 defining a device identifier, receivable commands and device outputs. The receivable commands are inputs which the autonomous device is responsive to, such as a request for a parameter, and are accompanied by a length field. The device outputs are published to the exchange for receipt by another autonomous device, typically based on the type of device and a timing interval or as a response to a command. The exchange 130 stores, for each device 110 of the plurality of autonomous devices 110-N, the device specification, as disclosed at step 201. The server 132 stores the device specification 150 for retrieval by another device 110. The exchange 130 also publishes at least a portion of the stored device specification for receipt by at least one other of the autonomous devices, as depicted at step 202. This may be from a device 110 receiving the initial publication by the device 110, or may be retrieved from the server 132. The server 132 may also publish the portion of the device specification including only a device ID for indicating availability of the complete device specification 150.

Upon a time as determined by operation of the devices 110, the exchange 130 transmits, based on the published device specification 150, a message (165, FIG. 3) including a command or a device output from one of the autonomous devices 110 to a destination device 110' of the autonomous devices 110, such that the transmission is an unscripted exchange initiated by the transmitting autonomous device 110 for receipt by the destination device 110' based on the published device specification from the destination device 110'. Note that any of the autonomous devices 110 could be a destination, or recipient device 110' based on the device ID. The unscripted nature allows the message to be received by the destination device 110' based only on the device specification indicating field position. It need not parse to find positional references encoded into the message as in a protocol having hierarchical, conditional and nested fields arranged in layers, for example.

Figure 3:
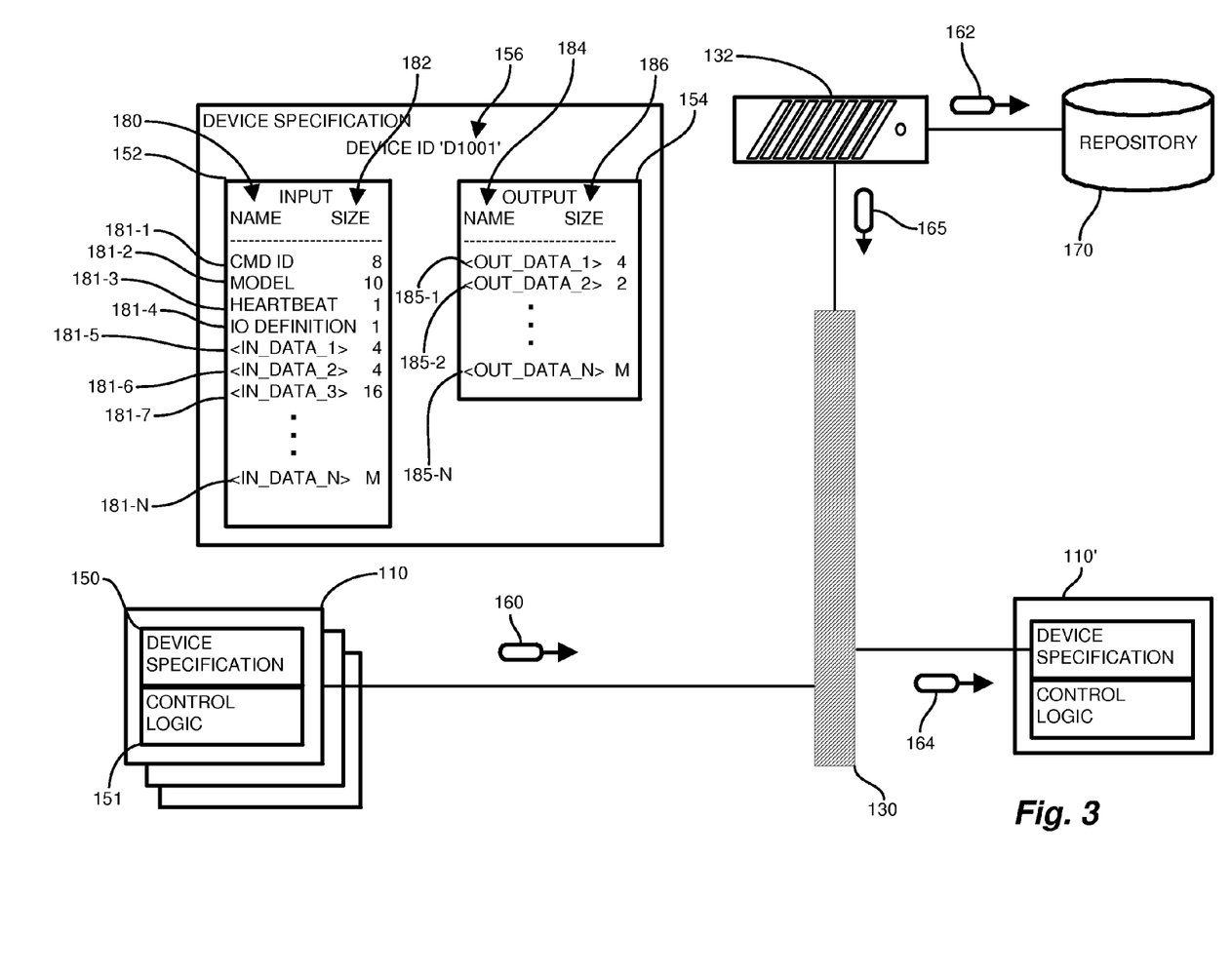
FIG. 3 is a block diagram of a device specification for exchanging control and data as in FIG. 2.

FIG. 3 is a block diagram of a device specification for exchanging control and data as in FIG. 2. Referring to FIGS. 1 and 3, each autonomous device 110 has a device specification 150 for indicating the inputs (commands) 152 it will receive and the outputs 154 it can provide. The inputs identify commands and parameters which the device 110 is responsive to, and the outputs 154 specify data the device 110 will deliver (transmit) in response to a request command or at periodic intervals. Each device specification 150 also includes a unique device identifier 156 for identifying the corresponding device 110. Upon startup or connection to the exchange 130, each device 110 sends a message 160 including its device specification 150 to the server 132. The server stores 162 the device specification 150 in a repository 170, and also makes the device specification 150 available to other devices 110 by demand or refresh messages 165. Each device 110 also has control logic 151 for defining how the device responds to other devices 110 of a particular type or ID. For example, in an arrangement of devices 110 including a surgical pump and shaver system, the shaver may include logic to look for a device of a pump type, and the pump and shaver may look for a device 110 of a monitor type for displaying shaver speed and pump pressure to a doctor or other personnel 118.

Each device specification 150, therefore, defines a set of inputs 152 and outputs 154. The inputs 152 include a list of input fields 180 and a corresponding length 182, and the outputs include a list of output fields 184 and length (size) 184. While the individual fields may include a delimiter or length, the device specification indicates allowable (expected) fields. For input, which includes commands, the list 180 includes a command ID 181-1 indicating a particular instruction or request for which the device 110 is responsive, and a model 181-2 to indicate the type of device (i.e. a pump or shaver, in the example above). Also included is a heartbeat signal 181-3, which is typically sent from the server 132 to ensure the device is operational, and an IO definition 181-4 that defines the number of input 180 fields and output fields 184, and the maximum length of each field 180, 184. The remaining input fields 181-5 . . . 185-N (185 generally) include other parameters or data related to the command 181-1. The input 152 further includes a set of input fields 181-5 . . . 181-N (181 generally) for specifying parameters corresponding to the command in the command ID field 181-1. The output includes a similar set of output fields 185-1 . . . 185-N (185 generally), which may be in response to a particular command 181 or may be sent periodically. The control logic 151 defines the commands 181-1 the device 110 receives and how to process each command, such as the outputs to 185 provide for a particular command. In general, each message corresponds to the device specification 150 of the device so that each of the fields 180, 184 occupies a similar position so that parsing is avoided. In a particular configuration, the device specification may include null or unused fields to maintain positioning of fields, in contrast to network protocols and TLV (type, length, value) formats which must be sequentially parsed in entirety and mapped to field definitions for data value identification. For example, the shaver may periodically send a speed (RPM) update to the pump and the monitor (GUI), and be responsive to an increase or decrease command from the GUI for changing the speed. The pump may employ control logic 151 to respond proportionally to the speed, or may receive explicit commands from the GUI to increase or decrease pressure.

Figure 4:
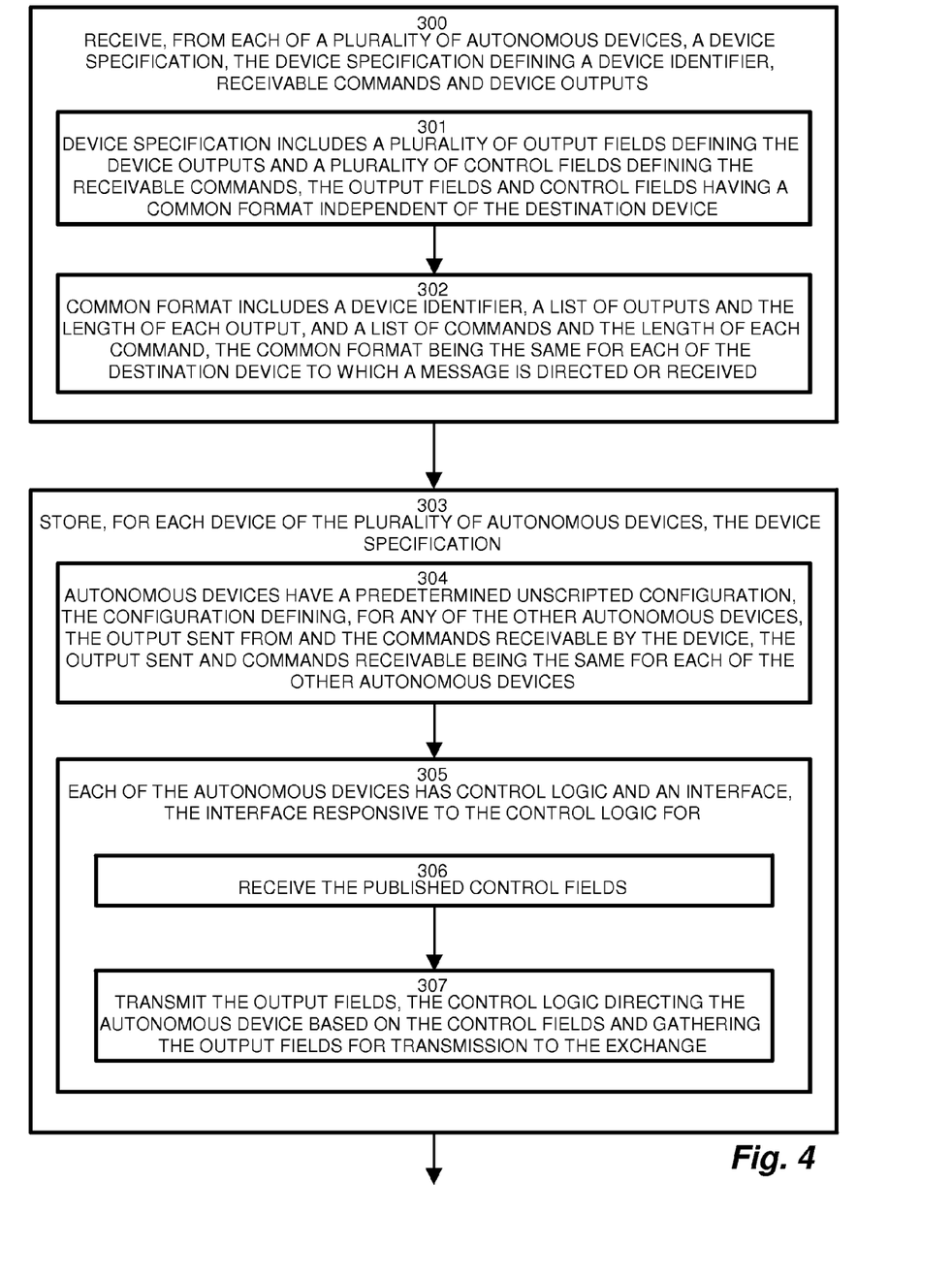
FIGS. 4-6 are a flowchart of employing the device specification with the exchange in greater detail.
Figure 5:
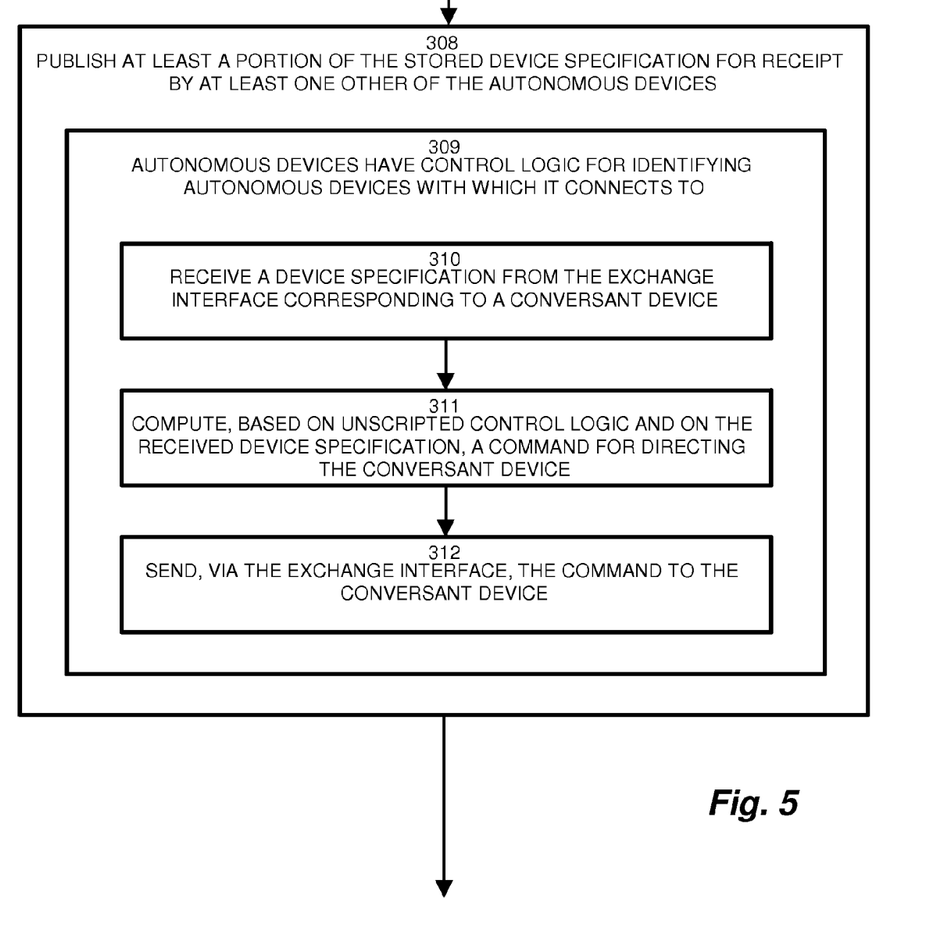
Figure 6:
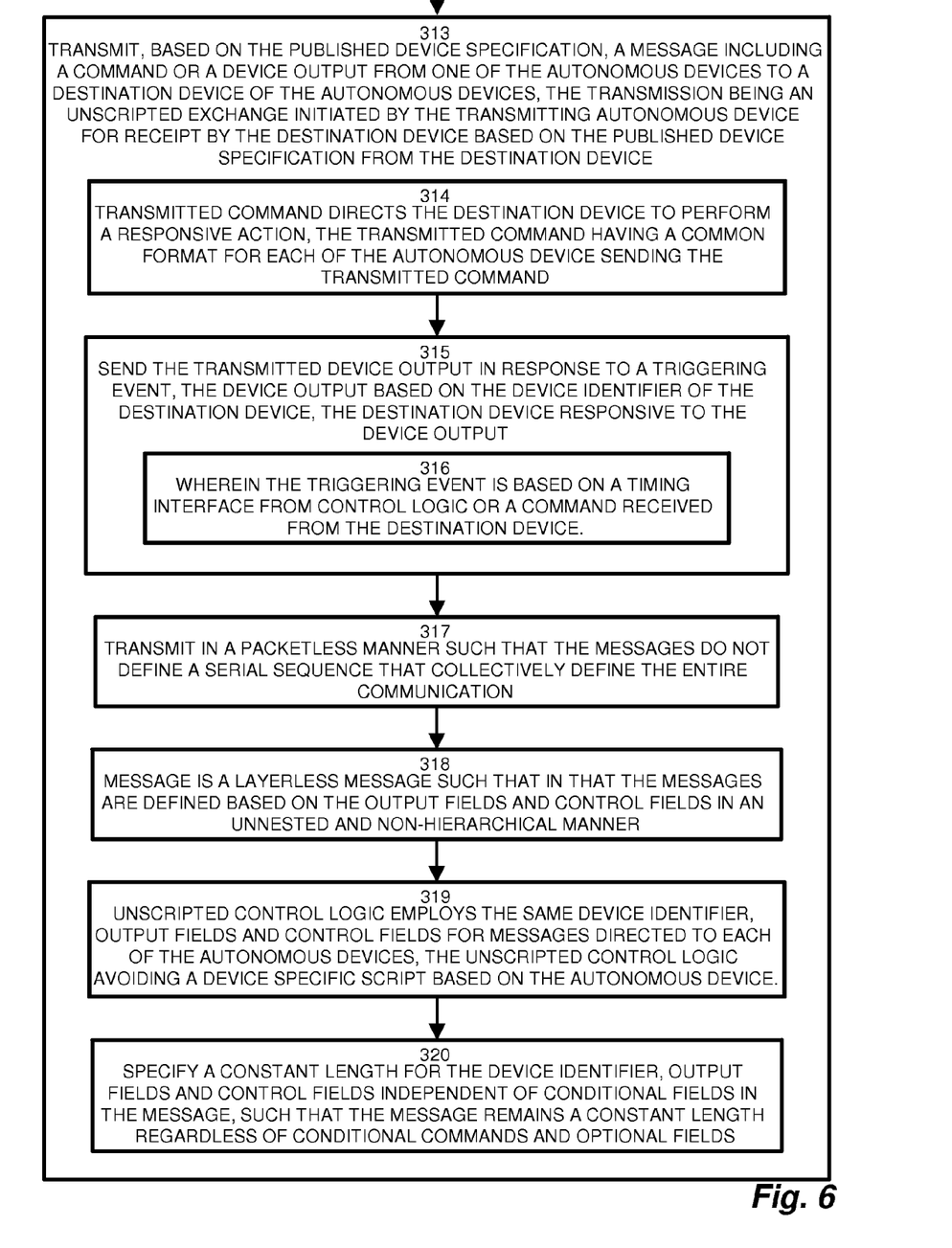

FIGS. 4-6 are a flowchart of employing the device specification with the exchange in greater detail. Referring to FIGS. 1 and 3-6, the exchange 130 receives, from each of a plurality of autonomous devices, a device specification, in which the device specification defines a device identifier, receivable commands and device outputs, as depicted at step 300. The device specification includes a plurality of output fields defining the device outputs and a plurality of control fields defining the receivable commands, such that the output fields and control fields having a common format independent of the destination device, as depicted at step 301. The common format is shared by each of the autonomous devices 110 and includes a device identifier, a list of outputs 184 and the length 186 of each output, and a list of commands 180 and the length 182 of each command, as disclosed at step 302. The common format is the same for each of the destination device to which a message is directed or received such that protocol identification, scripts or translations are not needed for receipt.

The server 132 stores, for each device 110 of the plurality of autonomous devices 110-N, the device specification 150 in the repository 170, as depicted at step 303. By storing and publishing the device specification 150, each of the autonomous devices 110 has access to a predetermined unscripted configuration that defines, for any of the other autonomous devices, the output sent from and the commands receivable by the device, such that the output sent and commands receivable being the same for each of the other autonomous devices 110, as disclosed at step 304. In other words, the device specification 150 defines a particular structure for a command regardless of the autonomous device from which it emanates, rather than different command structures employed in conventional approaches when the devices respond to different protocols or transport mediums.

Each of the autonomous devices 110 has control logic 151 and an interface 111, as depicted at step 305, such that the interface 111 is responsive to the control logic for receiving the published control fields 152 according to the device specification 150, as shown at step 306, and transmitting the output fields 154, the control logic 151 directing the autonomous device 110 based on the control fields 152 and gathering the output fields for transmission to the exchange 130, as depicted at step 307.

In order for an autonomous device 110 to send to another, recipient autonomous device 110', the server 132 publishes, via the exchange 130, at least a portion of the stored device specification 150 for receipt by at least one other of the autonomous devices, as disclosed at step 308. Each of the autonomous devices has control logic 151 for identifying autonomous devices 110 with which it connects to, as disclosed at step 309, such that transmitting further includes receiving 150' a device specification 150 from the exchange interface 130 corresponding to a conversant device 110, such as the destination device 110' to which a command 180 (input) is to be sent, as shown at step 310. The sending device 110 computes, based on unscripted control logic 151 and on the received device specification 150, a command 181-1 for directing the conversant device 110', as disclosed at step 311. The sending device 110 then sends, via the exchange interface 130, the command 164 to the conversant device 110, as depicted at step 312.

In the example given above, the operator 118 may use the console device 110-101 to send to the shaver to reduce RPMs. The shaver 110 then sends a message to the pump 110' to reduce pressure a corresponding amount. Various control scenarios may be envisioned by those of skill in the art. The exchange 130 transmits, based on the published device specification 150', a message 164 including a command or a device output from one of the autonomous devices 110 to a destination device 110' of the autonomous devices 110, such that the transmission is an unscripted exchange initiated by the transmitting autonomous device 110 for receipt by the destination device 110' based on the published device specification 150 from the destination device 110', as described at step 313. The transmitted command 164 directs the destination device 110' to perform a responsive action, in which the transmitted command 164 has a common format for each of the autonomous devices 110 sending the transmitted command, as disclosed at step 314, because it is based on the device specification 150 of the destination device 110'.

In the example arrangement, the message may be sent in response to a triggering event, in which the device output 184 is based on the device identifier 156 of the destination device 110', such that the destination device 110' is responsive to the device output 154, as depicted at step 315. The message 164 may result from a triggering event based on a timing interface from the control logic 151 or a command 164 received from the destination device 151' as shown at step 316. Transmitting the message may further includes transmitting in a packetless manner such that the messages 164 do not define a serial sequence that collectively define the entire communication (i.e. as a series of payloads to be reassembled), as depicted at step 317. The device specification may define each command to fit within a single transmission, or message, thus relieving the need for multiple packets. Conventional serial or packet switched mediums define a payload and header, and may subdivide a message into noncontiguous segments for transmission as payload in a sequence of packets. In contrast, the claimed commands and outputs define contiguous transmissions based on the device specification. Further, the message 164 is a layerless message such that in that the messages are defined based on the output fields 154 and command (input) fields 152 in an untested and non-hierarchical manner, as disclosed at step 318, in contrast to conventional protocols which define a hierarchy of nested, variable length fields and tags.

The unscripted control logic 151 employs the same device identifier, output fields and control fields for messages directed to each of the autonomous devices 110, such that the unscripted control logic avoids a device specific script based on the autonomous device 110, as depicted at step 319. In the example arrangement, the device specification 150 specifies a constant length for the device identifier, output fields and control fields independent of conditional fields in the message, such that the message remains a constant length regardless of conditional commands and optional fields, as depicted at step 320.

Those skilled in the art should readily appreciate that the programs and methods for performing control and data exchange between autonomous devices as defined herein are deliverable to a user processing and rendering device in many forms, including but not limited to a) information permanently stored on non-writeable storage media such as ROM devices, b) information alterably stored on writeable non-transitory storage media such as floppy disks, magnetic tapes, CDs, RAM devices, and other magnetic and optical media, or c) information conveyed to a computer through communication media, as in an electronic network such as the Internet or telephone modem lines. The operations and methods may be implemented in a software executable object or as a set of encoded instructions for execution by a processor responsive to the instructions. Alternatively, the operations and methods disclosed herein may be embodied in whole or in part using hardware components, such as Application Specific Integrated Circuits (ASICs), Field Programmable Gate Arrays (FPGAs), state machines, controllers or other hardware components or devices, or a combination of hardware, software, and firmware components.

While the system and method of performing control and data exchange between autonomous devices has been particularly shown and described with references to embodiments thereof, it will be understood by those skilled in the art that various changes in form and details may be made therein without departing from the scope of the invention encompassed by the appended claims.

What is claimed is:

1. A method of control and data exchange between autonomous devices comprising:
receiving, from each of a plurality of autonomous devices, a device specification, the device specification defining a device identifier, receivable commands and device outputs;
storing, for each device of the plurality of autonomous devices, the device specification in a common location accessible to each of the autonomous devices for asynchronous access;
publishing at least a portion of the stored device specification for receipt by at least one other of the autonomous devices; and
transmitting, based on the published device specification, a message including a command or a device output from one of the autonomous devices to a destination device of the autonomous devices, the transmission being an unscripted exchange initiated by the transmitting autonomous device for receipt by the destination device based on the published device specification from the destination device, the device specification including a plurality of output fields defining the device outputs and a plurality of control fields defining the receivable commands, the output fields and control fields having a common format independent of the destination device, further comprising
transmitting the commands and device specification over a common bus readable by all connected devices, wherein each device reads and interprets based on an identifier rather than visibility of the command,
the message including a device identifier designating the recipient device,
the device identifier configured to be read by the recipient and compared to the identification of the recipient;
specifying a constant length for the device identifier, output fields and control fields independent of conditional fields in the message, such that the message remains a constant length regardless of conditional commands and optional fields;
reading, at the recipient device, the device identifier;
comparing the device identifier to the identity of the recipient device; and
responding to the command in the message if the device identifier matches the identity, the transmitted message accessible to the recipient device based on indexing from the device specification, without parsing according to a protocol and variable length payload.

2. The method of claim 1 wherein the transmitted message includes a command that directs the destination device to perform a responsive action, the transmitted command having a common format for each of the autonomous device sending the transmitted command.

3. The method of claim 2 wherein the common format includes the device identifier, a list of outputs and the length of each output, and a list of commands and the length of each command, the common format being the same for each of the destination device to which a message is directed or received.

4. The method of claim 1 wherein transmitting further comprises:
sending the transmitted device output in response to a triggering event, the device output based on the device identifier of the destination device, the destination device responsive to the device output.

5. The method of claim 4 wherein the triggering event is based on a timing interface from control logic or a command received from the destination device.

6. The method of claim 1 wherein transmitting the message further comprises transmitting a currently stored device specification in a single message that defines the entire communication.

7. The method of claim 6 wherein the message is a layerless message such that in that the messages are defined based on the output fields and control fields in an unnested and non-hierarchical manner.

8. The method of claim 1 wherein each of the autonomous devices has control logic and an interface, the interface responsive to the control logic for:
receiving the published control fields; and
transmitting the output fields, the control logic directing the autonomous device based on the control fields and gathering the output fields for transmission to the exchange.

9. The method of claim 1 wherein the autonomous devices have control logic for identifying autonomous devices with which it connects to, transmitting further comprising:
receiving a device specification from the exchange interface corresponding to a conversant device;
computing, based on unscripted control logic and on the received device specification, a command for directing the conversant device; and
sending, via the exchange interface, the command to the conversant device.

10. The method of claim 9 wherein the unscripted control logic employs the same device identifier, output fields and control fields for messages directed to each of the autonomous devices, the unscripted control logic avoiding a device specific script based on the autonomous device.

11. The method of claim 1 wherein the autonomous devices have a predetermined unscripted configuration, the configuration defining, for any of the other autonomous devices, the output sent from and the commands receivable by the device, the output sent and commands receivable being the same for each of the other autonomous devices.

12. A system for unscripted integration and control between interconnected devices, comprising:
a plurality of autonomous devices each having a device specification;
an exchange interface coupled to each of the plurality of autonomous devices, the exchange interface responsive to each of the autonomous devices for storing the device specifications in a common location accessible to each of the autonomous devices for asynchronous access and transmitting the device specification to others of the autonomous devices; and
each of the autonomous devices having control logic, the control logic for
transmitting, based on the published device specification, a message including a command or a device output from one of the autonomous devices to a destination device of the autonomous devices, the transmission being an unscripted exchange initiated by the transmitting autonomous device for receipt by the destination device based on the published device specification from the destination device, the device specification including a plurality of output fields defining the device outputs and a plurality of control fields defining the receivable commands, the output fields and control fields having a common format independent of the destination device, further comprising
transmitting the commands and device specification over a common bus readable by all connected devices, wherein each device reads and interprets based on an identifier rather than visibility of the command,
the message including a device identifier designating the recipient device,
the device identifier configured to be read by the recipient and compared to the identification of the recipient;
specifying a constant length for the device identifier, output fields and control fields independent of conditional fields in the message, such that the message remains a constant length regardless of conditional commands and optional fields;
reading, at the recipient device, the device identifier;
comparing the device identifier to the identity of the recipient device; and
responding to the command in the message if the device identifier matches the identity, the transmitted message accessible to the recipient device based on indexing from the device specification, without parsing according to a protocol and variable length payload.

13. The system of claim 12 wherein the transmitted message includes a command that directs the destination device to perform a responsive action, the transmitted message having a common format for each of the autonomous device sending the transmitted command, wherein the common format includes a device identifier, a list of outputs and the length of each output, and a list of commands and the length of each command, the common format being the same for each of the destination device to which a message is directed or received.

14. The system of claim 12 wherein transmitting the message further comprises transmitting a device specification from a first autonomous device to the exchange, and transmitting from the exchange to a second autonomous device.

15. The system of claim 14 wherein the message maps fields from the device specification such that in that the messages are defined based on the output fields and control fields in an unnested and non-hierarchical manner.

16. The system of claim 15 wherein the unscripted control logic employs the same device identifier, output fields and control fields for messages directed to each of the autonomous devices, the unscripted control logic avoiding a device specific script based on the autonomous device.

17. In a medical device environment, a non-transitory computer readable storage medium having logic encoded as instructions that when executed by a processor responsive to the instructions, perform a method of control and data exchange between autonomous devices, the method comprising:

receiving, from each of a plurality of autonomous devices, a device specification, the device specification defining a device identifier, receivable commands and device outputs;

storing, for each device of the plurality of autonomous devices, the device specification in a repository accessible to each of the autonomous devices for asynchronous access;

publishing at least a portion of the stored device specification for receipt by at least one other of the autonomous devices; and transmitting, based on the published device specification, a message including a command or a device output from one of the autonomous devices to a destination device of the autonomous devices, the transmission being an unscripted exchange initiated by the transmitting autonomous device for receipt by the destination device based on the published device specification from the destination device, the device specification including a plurality of output fields defining the device outputs and a plurality of control fields defining the receivable commands, the output fields and control fields having a common format independent of the destination device, further comprising transmitting the commands and device specification over a common bus readable by all connected devices, wherein each device reads and interprets based on an identifier rather than visibility of the command, the message including a device identifier designating the recipient device, the device identifier configured to be read by the recipient and compared to the identification of the recipient;

specifying a constant length for the device identifier, output fields and control fields independent of conditional fields in the message, such that the message remains a constant length regardless of conditional commands and optional fields;

reading, at the recipient device, the device identifier;

comparing the device identifier to the identity of the recipient device; and responding to the command in the message if the device identifier matches the identity, the transmitted message accessible to the recipient device based on indexing from the device specification, without parsing according to a protocol and variable length payload.

18. The method of claim 1 wherein the device specification defines field positions such that similar fields are in similar positions such that sequential parsing for identifying fields is avoided.

* * * * *